United States Patent [19]

Rondeau et al.

[11] Patent Number: 5,993,490
[45] Date of Patent: *Nov. 30, 1999

[54] COMPOSITION FOR THE OXIDATION DYEING OF KERATIN FIBERS CONTAINING A CATIONIC DIRECT DYE AND DYEING PROCESS USING THIS COMPOSITION

[75] Inventors: Christine Rondeau, Sartrouville; Jean Cotteret, Verneuil Sur Seine; Roland de la Mettrie, le Vesinet, all of France

[73] Assignee: L'Oreal, France

[*] Notice: This patent is subject to a terminal disclaimer.

[21] Appl. No.: 08/994,130

[22] Filed: Dec. 19, 1997

[30] Foreign Application Priority Data

Dec. 23, 1996 [FR] France .................. 96 15891

[51] Int. Cl.$^6$ ............................ A61K 7/13
[52] U.S. Cl. .................. 8/409; 8/407; 8/408; 8/410; 8/426
[58] Field of Search .............. 8/405, 406, 407, 8/408, 409, 410, 423, 424, 426

[56] References Cited

U.S. PATENT DOCUMENTS

| | | | |
|---|---|---|---|
| 3,524,842 | 8/1970 | Grossman et al. | 8/426 |
| 3,578,386 | 5/1971 | Kalopissis et al. | 8/426 |
| 3,869,454 | 3/1975 | Lang et al. | 534/778 |
| 3,985,499 | 10/1976 | Lang et al. | 8/426 |
| 4,025,301 | 5/1977 | Lang | 8/405 |
| 4,425,132 | 1/1984 | Grollier et al. | 8/405 |
| 5,637,115 | 6/1997 | Balzer et al. | 8/407 |
| 5,733,343 | 3/1998 | Mockli et al. | 8/426 |

FOREIGN PATENT DOCUMENTS 0 739 622  10/1996  European Pat. Off. .

*Primary Examiner*—Caroline D. Liott
*Attorney, Agent, or Firm*—Finnegan, Henderson, Farabow, Garrett & Dunner, L.L.P.

[57] ABSTRACT

A ready-to-use composition for the oxidation dyeing of keratin fibers, in particular human keratin fibers such as the hair, comprising at least one oxidation base selected from para-phenylenediamines and bis(phenyl)alkylenediamines, in combination with at least one coupler selected from meta-diphenols, at least one selected cationic direct dye and at least one oxidizing agent, as well as to the dyeing process using this composition.

41 Claims, No Drawings

COMPOSITION FOR THE OXIDATION DYEING OF KERATIN FIBERS CONTAINING A CATIONIC DIRECT DYE AND DYEING PROCESS USING THIS COMPOSITION

The technology involved in this application is related to that disclosed in the following U.S. applications filed on even data herewith:

(1) Title: COMPOSITION FOR THE OXIDATION DYEING OF KERATIN FIBERS AND DYEING PROCESS USING THIS COMPOSITION Inventors: Christine Rondeau, Jean Cotteret, Roland de la Mettrie Ser. No.:: 08/994,127, pending (2) Title: COMPOSITION FOR THE OXIDATION DYEING OF KERATIN FIBRES AND DYEING PROCESS USING THIS COMPOSITION Inventors: Christine Rondeau, Jean Cotteret, Roland de la Mettrie Ser. No.: 08/994,446, now U.S. Pat. No. 5,879,412

(3) Title: COMPOSITION FOR THE OXIDATION DYEING OF KERATIN FIBERS AND DYEING PROCESS USING THIS COMPOSITION Inventors: Christine Rondeau, Jean Cotteret, Roland de la Mettrie Ser. No. 08/994,444, pending The specifications of these related applications are hereby specifically incorporated by reference.

The present invention relates to a ready-to-use composition for the oxidation dyeing of keratin fibers, in particular human keratin fibers such as the hair, this composition comprising, in a medium which is suitable for dyeing, at least one oxidation base selected from para-phenylenediamines and bis(phenyl)alkylenediamines, in combination with at least one coupler chosen from meta-diphenols, at least one selected cationic direct dye and at least one oxidizing agent, as well as to the dyeing process using this composition. The invention also relates to a dyeing kit for the preparation of such a ready-to-use composition.

It is known to dye keratin fibers, and in particular human hair, with dye compositions containing oxidation dye precursors, in particular ortho- or para-phenylenediamines, and ortho- or para-aminophenols, which are generally referred to as oxidation bases. Oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or color modifiers, the latter being selected in particular from aromatic meta-diamines, meta-aminophenols, meta-diphenols and certain heterocyclic compounds.

The variety of compounds used as regards the oxidation bases and the couplers allows a wide range of colors to be obtained.

It is also known that in order to vary the shades obtained further and to give them glints, it is possible to use, in combination with the oxidation dye precursors and the couplers, direct dyes, i.e., colored substances which provide coloration in the absence of an oxidizing agent.

The so-called "permanent" coloration obtained by means of these oxidation dyes must moreover satisfy a certain number of requirements. Thus, it must be able to give shades of the desired intensity and it must be able to withstand external agents (light, bad weather, washing, permanent waving, perspiration, rubbing).

The great majority of direct dyes belong to the family of nitrobenzene compounds and have the drawback, when they are incorporated into dye compositions, of leading to colorations that have insufficient endurance, i.e., fastness, in particular with respect to shampoos.

The present invention is aimed at proposing novel compositions for the oxidation dyeing of keratin fibers, and in particular human keratin fibers such as the hair, which make it possible to obtain radiant colorations with good endurance properties.

Thus, the inventors have discovered that it is possible to obtain novel dyes that are both radiant and have good endurance by combining:

at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye selected from the compounds of formulae (I), (I') and (II) below, and at least one oxidizing agent.

The first subject of the invention is thus a ready-to-use composition for the oxidation dyeing of deratin fibers, and in particular human keratin fibers such as the hair, characterized in that it comprises, in a medium which is suitable for dyeing:

at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye selected from:

a) the compounds of formulae (I) and (I') below:

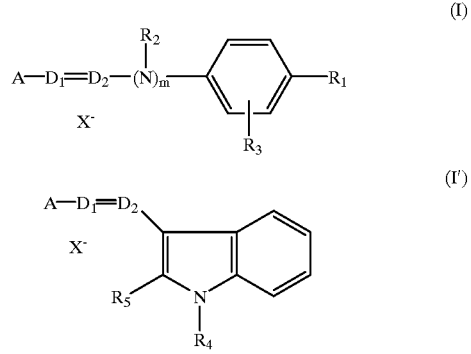

in which:

$R_1$ represents a hydrogen atom, a $C_1$–$C_4$ alkoxy radical, a halogen atoms such as bromine, chlorine, iodine or fluorine, or an amino radical, $R_2$ represents a hydrogen atom, a $C_1$–$C_4$ alkyl radical or forms, with a carbon atom of the benzene ring, a heterocycle which is optionally oxygenated and/or substituted with one or more $C_1$–$C_4$ alkyl groups, $R_3$ represents a hydrogen or halogen atom such as bromine, chlorine, iodine or fluorine, $R_4$ and $R_5$ each independently represents a hydrogen atom or a $C_1$–$C_4$ alkyl radical, $D_1$ and $D_2$ each independently represents a nitrogen atom or the —CH group, m=0 or 1, it being understood that when $R_1$ represents an unsubstituted amino group, then $D_1$ and $D_2$ simultaneously represent a —CH group and m=0, X represents an anion preferably selected from chloride, methylsulphate and acetate, A represents a group selected from the structures A1 to A8 below:

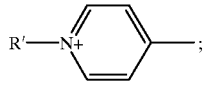
A1

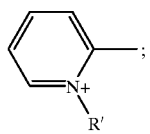
A2

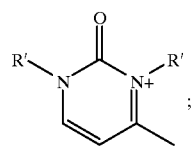
A3

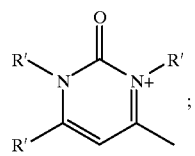
A4

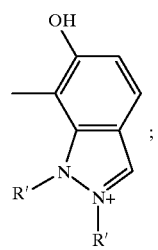
A5

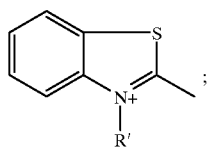
A6

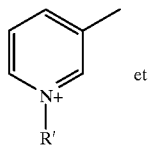
A7

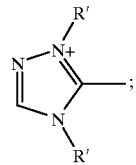
A8 in which:

R¹ represents a $C_1$–$C_4$ alkyl radical;

when m=0 and $D_1$ represents a nitrogen atom, then A can also denote a group of structure A9 below:

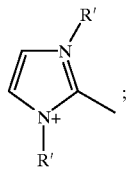
A9 in which:

R' represents a $C_1$–$C_4$ alkyl radical;

b) the compounds of formula (II) below:

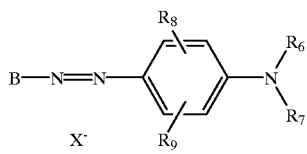
(II)

in which:

$R_6$ represents a hydrogen atom or a $C_1$–$C_4$ alkyl radical, $R_7$ represents a hydrogen atom, an alkyl radical which may be substituted with a —CN radical or an amino group or a 4'-aminophenyl radical or forms with $R_6$ a heterocycle which is optionally oxygenated and/or nitrogenous, which may be substituted with one or more $C_1$–$C_4$ alkyl groups, $R_8$ and $R_9$ each independently represent a hydrogen atom, a halogen atom such as bromine, chlorine, iodine or fluorine, a $C_1$–$C_4$ alkyl radical, a $C_1$–$C_4$ alkoxy radical or a —CN radical, X⁻ represents an anion preferably selected from chloride, methylsulphate and acetate, B represents a group selected from the structures B1 to B11 below:

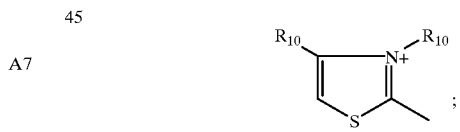
B1

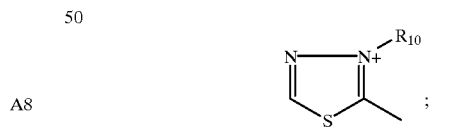
B2

B3

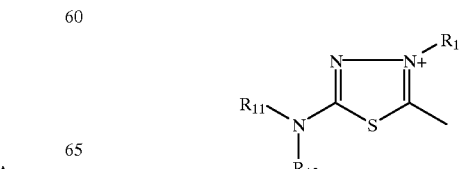
B4

-continued

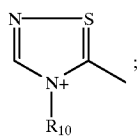
B5

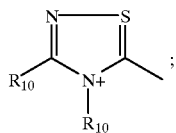
B6

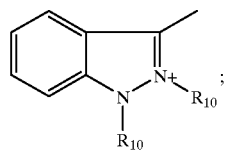
B7

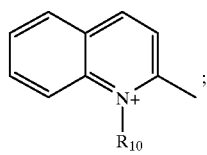
B8

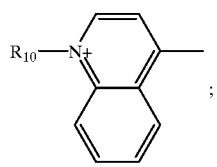
B9

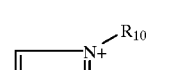
B10 et

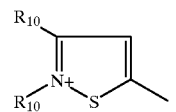
B11 in which:

$R_{10}$ represents a $C_1$–$C_4$ alkyl radical, $R_{11}$ and $R_{12}$ each independently represent a hydrogen atom or a $C_1$–$C_4$ alkyl radical;

when $R_6$ and $R_7$ form a nitrogenous heterocycle, or when $R_8$ and $R_9$ simultaneously represent a $C_1$–$C_4$ alkoxy radical, or when $R_7$ represents a 4'-aminophenyl radical, then B can also represent a group of structure B12 below:

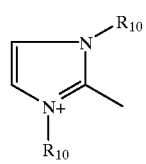
B12 in which $R_{10}$ has the same meaning as that indicated above for the structures B1 to B11; and
at least one oxidizing agent.

The ready-to-use dye compositions in accordance with the invention make it possible to obtain colorations in pearlescent, ash or golden natural shades which effectively withstand the various treatments to which the hair may be subjected and in particular with regard to shampoos.

A subject of the invention is also a process for the oxidation dyeing of keratin fibers using this ready-to-use dye composition.

The para-phenylenediamines which can be used as oxidation bases in ready-to-use dye compositions in accordance with the invention are preferably selected from the compounds of formula (III) below, and the acid-addition salts thereof:

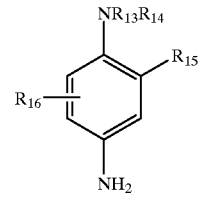
(III)

in which:

$R_{13}$ represents a hydrogen atom, a $C_1$–$C_4$ alkyl, $C_1$–$C_4$ monohydroxyalkyl, $C_2$–$C_4$ polyhydroxyalkyl, phenyl, 4'-aminophenyl or $(C_1$–$C_4)$alkoxy$(C_1$–$C_4)$alkyl radical, $R_{14}$ represents a hydrogen atom or a $C_1$–$C_4$ alkyl, $C_1$–$C_4$ monohydroxyalkyl or $C_2$–$C_4$ polyhydroxyalkyl radical, $R_{15}$ represents a hydrogen atom, a halogen atom such as a chlorine, bromine, iodine or fluorine atom, or a $C_1$–$C_4$ alkyl, $C_1$–$C_4$ monohydroxyalkyl, $C_1$–$C_4$ hydroxyalkoxy, $C_1$–$C_4$ mesylaminoalkoxy, $C_1$–$C_4$ carbamoylaminoalkoxy or $C_1$–$C_4$ acetylaminoalkoxy radical, $R_{16}$ represents a hydrogen atom or a $C_1$–$C_4$ alkyl radical.

Among the para-phenylenediamines of formula (III) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine and 2-β-acetylaminoethyloxy-para-phenylenediamine, and the acid-addition salts thereof.

Among the para-phenylenediamines of formula (III) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the acid-addition salts thereof are most particularly preferred.

The bis(phenyl)alkylenediamines which can be used as oxidation base in the ready-to-use dye compositions in accordance with the invention are preferably selected from the compounds of formula (IV) below, and the acid-addition salts thereof:

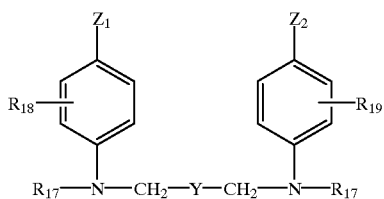
(IV)

in which:

$Z_1$ and $Z_2$ each independently represents a hydroxyl radical or $NHR_{20}$ in which $R_{20}$ represents a hydrogen atom or a $C_1$–$C_4$ alkyl radical, $R_{17}$ represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue can be substituted, $R_{18}$ and $R_{19}$ each independently represents a hydrogen or halogen atom or a $C_1$–$C_4$ alkyl radical, Y represents a radical selected from the following radicals:

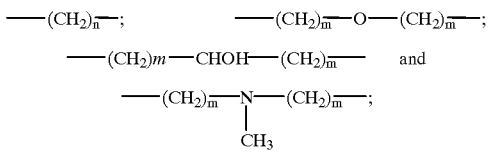

in which:

n is an integer ranging from 0 to 8 and m is an integer ranging from 0 to 4.

Among the bis(phenyl)alkylenediamines of formula (IV) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the acid-addition salts thereof.

Among these bis(phenyl)alkylenediamines of formula (IV), N,N'-bis(β-hydroxyethyl-N,N'-bis(4'-aminophenyl)-1,3-diaminopropanol or one of the acid-addition salts thereof is particularly preferred.

The meta-diphenols which can be used as couplers in the ready-to-use dye compositions in accordance with the invention are preferably selected from the compounds of formula (V) below, and the acid-addition salts thereof:

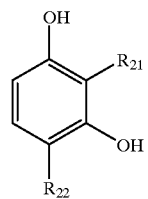
(V)

in which:

$R_{21}$ and $R_{22}$ each independently represent a hydrogen atom, a $C_1$–$C_4$ alkyl radical or a halogen atom selected from chlorine, bromine and fluorine.

Among the meta-diphenols of formula (V) above, mention may be made more particularly of 1,3-dihydroxybenzene, 2-methyl-1,3-dihydroxybenzene, 4-chloro-1,3-dihydroxybenzene and 2-chloro-1,3-dihydroxybenzene, and the acid-addition salts thereof.

The cationic direct dyes of formulae (I), (I') and (II) which can be used in the ready-to-use dye compositions in accordance with the invention are known compounds and are described, for example, in patent applications WO 95/01772, WO 95/15144 and EP-A-0 714 954, the disclosures of which are specifically incorporated by reference herein.

Among the cationic direct dyes of formula (I) which can be used in the ready-to-use dye compositions in accordance with the invention, mention may be made more particularly of the following compounds corresponding to structures (I1) to (I18) below:

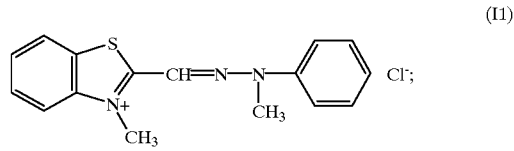
(I1)

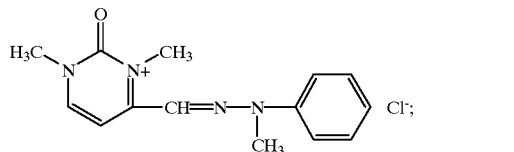
(I2)

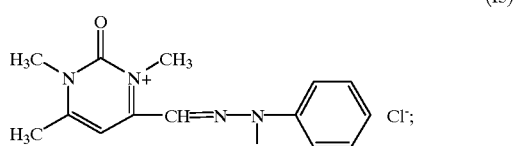
(I3)

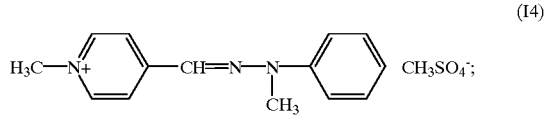
(I4)

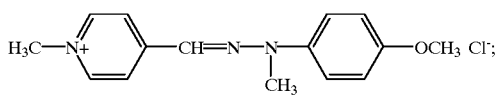
(I5)

-continued (I6) [structure: H₃C—N⁺(pyridine)—CH=N—N(indoline) CH₃SO₄⁻;]

(I7) [structure: H₃C—N⁺(pyridine)—CH=N—N(2,2,3,3-tetramethylindoline) CH₃SO₄⁻;]

(I8) [structure: H₃C—N⁺(pyridine)—CH=N—N(CH₃)(2-fluorophenyl) Cl⁻;]

(I9) [structure: H₃C—N⁺(pyridine)—CH=N—N(CH₃)(4-chlorophenyl) Cl⁻;]

(I10) [structure: 1-methyl-2-pyridinium—CH=N—N(CH₃)(phenyl) CH₃SO₄⁻;]

(I11) [structure: 1-methyl-2-pyridinium—CH=N—N(indoline) CH₃SO₄⁻;]

(I12) [structure: 1-methyl-2-pyridinium—CH=N—N(CH₃)(4-chlorophenyl) CH₃SO₄⁻;]

(I13) [structure: H₃C—N⁺(pyridine)—CH=N—N(CH₃)(4-methoxyphenyl) CH₃SO₄⁻;]

(I14) [structure: 1,3-dimethylimidazolium-2-yl—N=N—(4-methoxyphenyl) Cl⁻;]

(I15) [structure: 1-methyl-2-pyridinium—CH=CH—(4-aminophenyl) NH₂ CH₃COO⁻;]

(I16) [structure: H₃C—N⁺(pyridine)—CH=CH—(4-aminophenyl) NH₂ CH₃COO⁻;]

(I17) [structure: H₃C—N⁺(pyridine)—CH=N—N(CH₃)(phenyl) Cl⁻;]

and (I18) [structure: 1,2-dimethyl-1H-indazolium with OH and 4-chlorophenylazo substituents, Cl⁻.]

Among the cationic direct dyes of formula (I') which can be used in the ready-to-use dye compositions in accordance with the invention, mention may be made more particularly of the compounds corresponding to structures (I'1) to (I'3) below:

(I'1) [structure: 1-methylpyridinium-3-yl—N=N—(2-methyl-1H-indol-3-yl) Cl⁻;]

(I'2) [structure: 1-methyl-4-pyridinium—CH=CH—(1H-indol-3-yl) Cl⁻;]

and (I'3) [structure: 1,4-dimethyl-1,2,4-triazolium-3-yl—N=N—(1-methyl-1H-indol-3-yl) Cl⁻.]

Among the cationic direct dyes of formula (II) which can be used in the ready-to-use dye compositions in accordance with the invention, mention may be made more particularly of the compounds corresponding to structures (II1) to (II26) below:

(II1) [structure: 1,3-dimethylimidazolium-2-yl—N=N—(4-phenyl)—NH—(4-aminophenyl) NH₂ Cl⁻;]

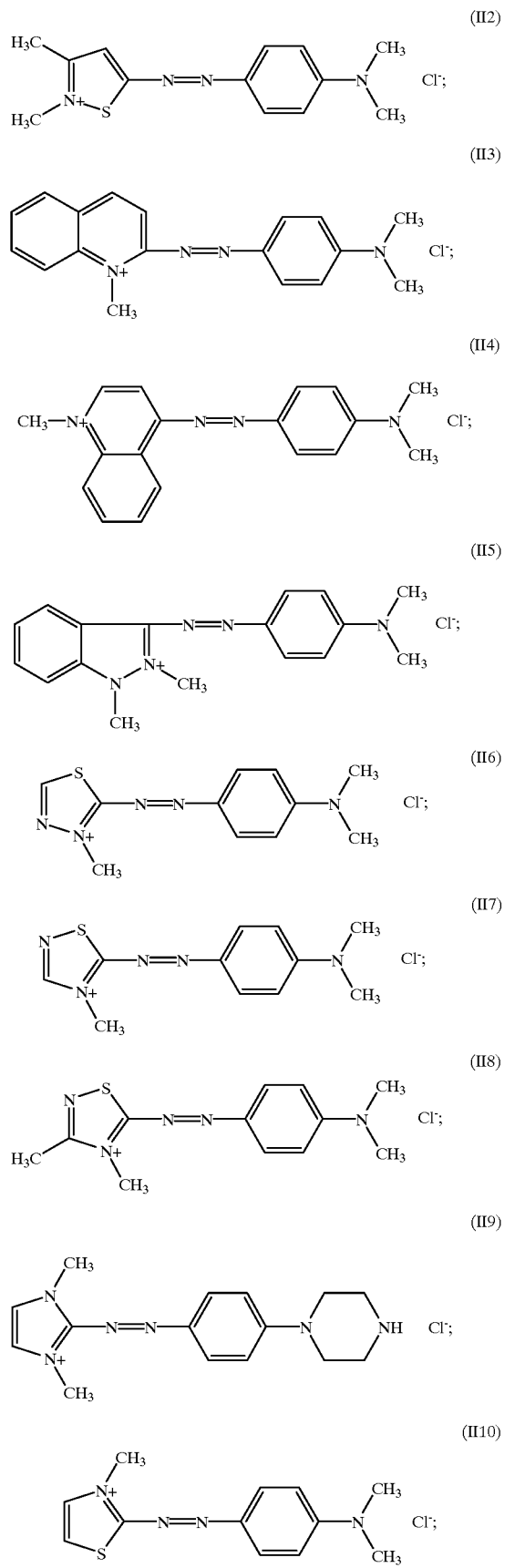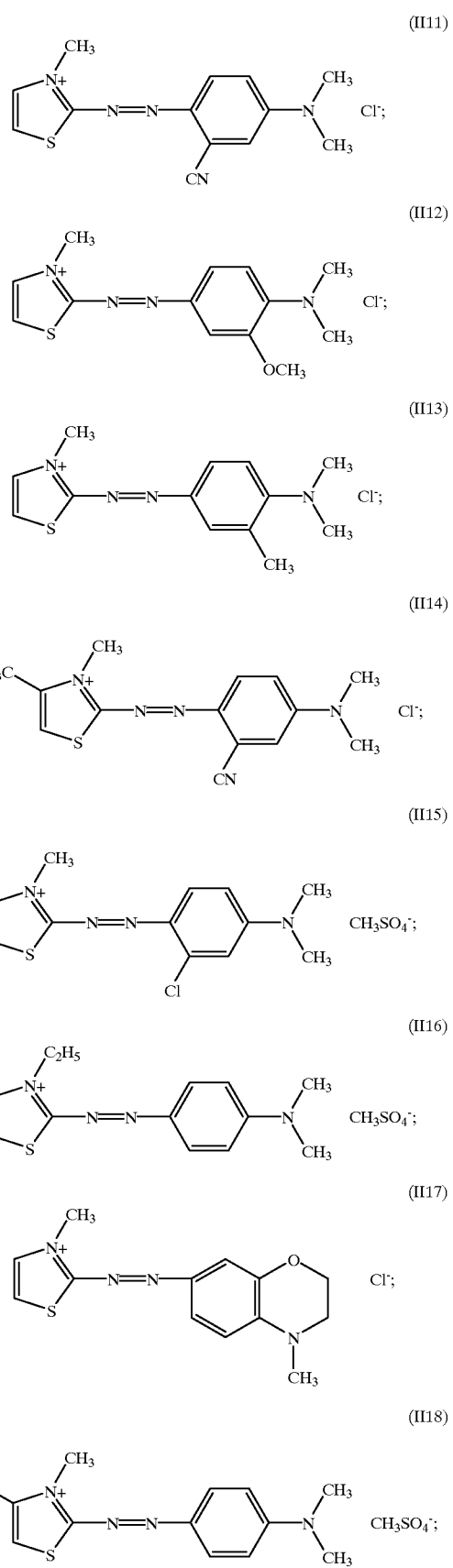

-continued

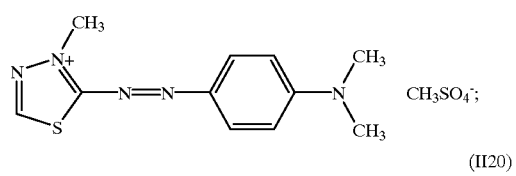
(II19)

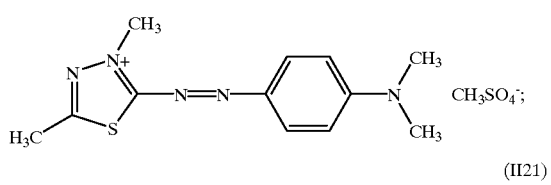
(II20)

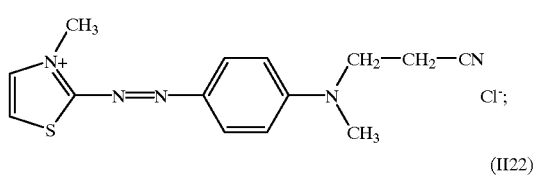
(II21)

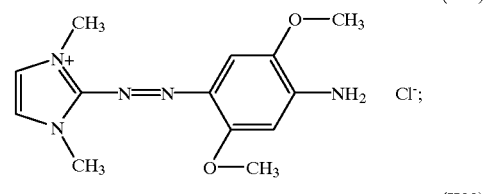
(II22)

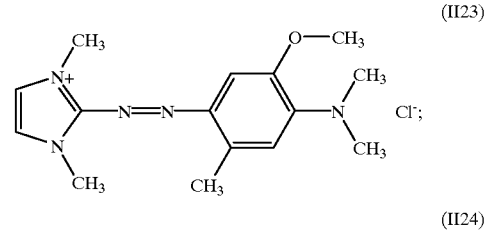
(II23)

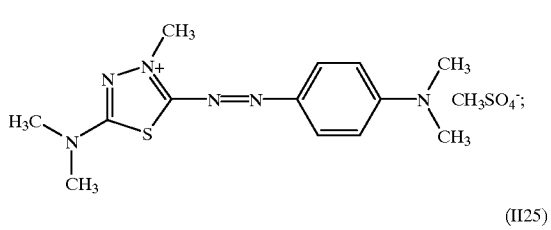
(II24)

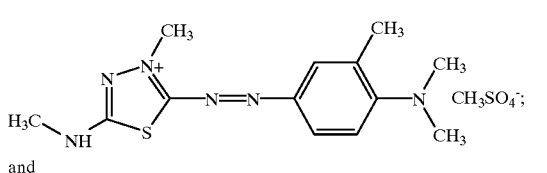
(II25)

and

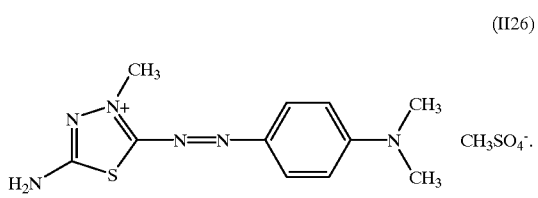
(II26)

Among the specific compounds of structures (I1) to (I18) described above, the compounds corresponding to structures (I4), (I5) and (I13) are more particularly preferred.

Among the specific compounds of structures (II1) to (II26) described above, the compound corresponding to structure (II1) is more particularly preferred.

The acid-addition salts which can be used in the context of the dye compositions of the invention are selected in particular from the hydrochlorides, carbonates, hydrobromides, sulphates and tartrates.

The oxidizing agent present in the dye composition is selected from the oxidizing agents used conventionally in oxidation dyeing and preferably from hydrogen peroxide, urea peroxide, alkali metal bromates and persalts such as perborates and persulphates. Hydrogen peroxide is particularly preferred.

The cationic direct dye(s) of formulae (I) and/or (I') and/or (II) in accordance with the invention preferably represent(s) from approximately 0.001 to approximately 10% by weight relative to the total weight of the ready-to-use dye composition, and even more preferably from approximately 0.05 to approximately 2% by weight relative to the total weight of the ready-to-use dye composition.

The oxidation base(s) in accordance with the invention, that is to say the para-phenylenediamine(s) of formula (III) and//or the bis(phenyl)alkylenediamine(s) of formula (IV), preferably represent(s) from approximately 0.0001 to approximately 10% by weight relative to the total weight of the ready-to-use dye composition, and even more preferably from approximately 0.001 to approximately 5% by weight relative to the total weight of the ready-to-use dye composition.

The meta-diphenol(s) of formula (V) in accordance with the invention preferably represent(s) from approximately 0.0001 to approximately 5% by weight relative to the total weight of the ready-to-use dye composition, and even more preferably from approximately 0.005 to approximately 3% by weight relative to the total weight of the ready-to-use dye composition.

The pH of the dye composition as defined above generally ranges from approximately 5 to 12. It can be adjusted to the desired value using acidifying or basifying agents usually used in the dyeing of keratin fibers.

Among the acidifying agents, mention may be made, by way of example, of inorganic or organic acids such as hydrochloric acid, orthophosphoric acid, carboxylic acids such as tartaric acid, citric acid or lactic acid, and sulphonic acids.

Among the basifying agents, mention may be made, by way of example, of aqueous ammonia, alkaline carbonates, alkanolamines such as mono-, di- and triethanolamines and derivatives thereof, sodium hydroxide, potassium hydroxide and the compounds of formula (VI) below:

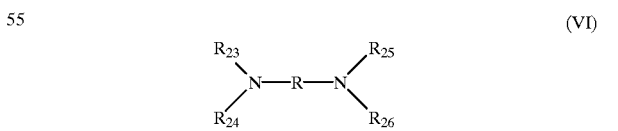
(VI)

in which:

R is a propylene residue optionally substituted with a hydroxyl group or a $C_1$–$C_4$ alkyl radical;

$R_{23}$, $R_{24}$, $R_{25}$ and $R_{26}$ each independently represent a hydrogen atom or a $C_1$–$C_4$ alkyl or $C_1$–$C_4$ hydroxyalkyl radical.

In addition to the dyes defined above, the dye composition in accordance with the invention can also contain other couplers and/or direct dyes, in particular in order to modify the shades or to enrich them with glints.

The medium which is suitable for dyeing (or the support) for the ready-to-use dye composition in accordance with the invention generally comprises water or a mixture of water and at least one organic solvent in order to dissolve the compounds which would not be sufficiently soluble in water. By way of organic solvent, mention may be made, for example, of $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably ranging from approximately 1 to approximately 40% by weight relative to the total weight of the dye composition, and even more preferably approximately 5 to approximately 30% by weight relative to the total weight of the dye composition.

The ready-to-use dye compositions in accordance with the invention can also contain various adjuvants used conventionally in compositions for dyeing the hair, such as anionic, cationic, nonionic or amphoteric surfactants or mixtures thereof, anionic, cationic, nonionic or amphoteric polymers or mixtures thereof, inorganic or organic thickeners, antioxidants, penetration agents, sequestering agents, fragrances, buffers, dispersing agents, packaging agents, film-forming agents, preserving agents and opacifiers.

Needless to say, a person skilled in the art will take care to select the optional additional compound(s) mentioned above such that the advantageous properties intrinsically associated with the ready-to-use dye composition in accordance with the invention are not, or are not substantially, adversely affected by the addition(s) envisaged.

The ready-to-use dye compositions in accordance with the invention can be in various forms, such as in the form of liquids, creams or gels or in any other form which is appropriate for dyeing keratin fibers, and in particular human hair.

A subject of the invention is also a process for dyeing keratin fibers, and in particular human keratin fibers such as the hair, using the ready-to-use dye composition as defined above.

According to this process, the ready-to-use dye composition as defined above is applied to the fibers and is left on them for an exposure time preferably of approximately 3 to approximately 40 minutes, even more preferably approximately 5 to approximately 30 minutes, after which the fibers are rinsed, optionally washed with shampoo, rinsed again and dried.

According to a first preferred embodiment, the process includes a preliminary step which involves separately storing, on the one hand, a composition (A) comprising, in a medium which is suitable for dyeing, at least one oxidation base selected from para-phenylenediamines, bis(phenyl) alkylenediamines, and the acid-addition salts thereof, at least one coupler selected from meta-diphenols, and the acid-addition salts thereof, and at least one cationic direct dye selected from the compounds of formulae (I), (I') and (II) as defined above, and, on the other hand, a composition (B) containing, in a medium which is suitable for dyeing, at least one oxidizing agent as defined above, and in mixing them together at the time of use before applying this mixture to the keratin fibers.

According to a second preferred embodiment, the process includes a preliminary step which involves separately storing, on the one hand, a composition (A) comprising, in a medium which is suitable for dyeing, at least one oxidation base selected from para-phenylenediamines, bis(phenyl) alkylenediamines, and the acid-addition salts thereof, at least one coupler selected from meta-diphenols, and the acid-addition salts thereof; on the other hand, a composition (A') comprising, in a medium which is suitable for dyeing, at least one cationic direct dye selected from the compounds of formulae (I), (I') and (II) as defined above; and, lastly, a composition (B) containing, in a medium which is suitable for dyeing, at least one oxidizing agent as defined above, and in mixing them together at the time of use before applying this mixture to the keratin fibers.

The composition (A') used according to this second variant of the process in accordance with the invention can optionally be in powder form, the cationic direct dye(s) of formulae (I) and/or (I') and/or (II) in accordance with the invention itself (themselves) constituting, in this case, all of the said composition (A') or optionally being dispersed in an organic and/or inorganic pulverulent excipient.

When it is present in the composition A', the organic excipient can be of synthetic or plant origin and is selected in particular from crosslinked and non-crosslinked synthetic polymers, polysaccharides such as celluloses and modified or unmodified starches, as well as natural products containing them such as sawdust and plant gums (guar gum, carob gum, xanthan gum, etc.).

When it is present in the composition (A'), the inorganic excipient can consist of metal oxides such as titanium oxides, aluminium oxides, kaolin, talc, silicates, mica and silicas.

An advantageous excipient preferred according to the invention is sawdust.

The powdered composition (A') can also contain binders or coating products in an amount which preferably does not exceed approximately 3% by weight relative to the total weight of the said composition (A').

These binders are preferably selected from oils and liquid fatty substances of inorganic, synthetic, animal or plant origin.

The composition (A') may optionally also contain other adjuvants, in powdered form, in particular surfactants of any nature, hair conditioners such as, for example, cationic polymers, etc.

Another subject of the invention is a multi-compartment dyeing "kit" or device or any other multi-compartment packaging system, a first compartment of which contains the composition (A) as defined above, an optional second compartment contains the composition (A') as defined above, when it is present, and a third compartment contains the oxidizing composition (B) as defined above. These devices can be equipped with means which allow the desired mixture to be applied to the hair, such as the devices described in French patent FR-2,586,913, the disclosure of which is specifically incorporated by reference herein.

The examples which follow are intended to illustrate the invention without, however, limiting its scope.

EXAMPLES 1 AND 2

Compositions 1 (A) and 2 (A) below, in accordance with the invention, were prepared (contents in grams):

| COMPOSITION | 1 (A) | 2 (A) |
|---|---|---|
| Para-phenylenediamine | 1.0 | 0.70 |
| 1,3-Dihydroxybenzene | 0.5 | 0.5 |
| Cationic dye of structure (II1) | 0.25 | — |
| Cationic dye of structure (I4) | 0.20 | — |
| Cationic dye of structure (I13) | — | 0.10 |
| Common dye support (*) | (*) | (*) |
| Water qs | 100 g | 100 g |

(*) Common dye support:

| | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name ETHOMEEN O12 by the company Akzo | 7.0 g |
| Diethylaminopropyl laurylaminosuccinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution containing 35% A.M. | 0.455 g A.M. |
| Ammonium acetate | 0.8 g |
| Antioxidant, sequestering agent | qs |
| Fragrance, preserving agent | qs |
| Aqueous ammonia containing 20% $NH_3$ | 10.0 g |

Each of these compositions 1 (A) and 2 (A) was mixed, at the time of use, with an equal amount of a composition (B) comprising a 20-volumes hydrogen peroxide solution (6% by weight).

Each resulting composition (ready-to-use composition in accordance with the invention) was applied for 30 minutes to locks of natural grey hair containing 90% white hairs. The locks of hair were then rinsed, washed with a standard shampoo and then dried.

The locks of hair were dyed in the shades given in the table below:

| EXAMPLE [COMPOSITION] | SHADE OBTAINED |
|---|---|
| 1 [1 (A)] | Dark chestnut |
| 2 [2 (A)] | Chestnut |

The shades obtained had very good endurance with respect to subsequent shampooing.

According to a variant of the invention, the cationic direct dyes can be incorporated into the dyeing compositions 1 (A) or 2 (A) at the time of use.

EXAMPLE 3

Composition 3 (A) below was prepared:
Para-toluylenediamine sulphate 1.25 g
2-Methyl-1,3-dihydroxybenzene 0.50 g
Common dye support as described above for Examples 1 (*) and 2
Demineralized water qs 100 g Composition 3 (A') below was prepared:
Cationic dye of structure (II1) 1 g
Quaternary polyammonium sold under the trade name 10 g Celquat SC-240 by the company National Starch
Sawdust qs 100 g One part by weight of composition 3 (A) above was mixed, at the time of use, with 0.1 part by weight of composition 3 (A') and with one part by weight of a composition (B) comprising a 20-volumes hydrogen peroxide solution (6% by weight).

The resulting composition was applied for 30 minutes to locks of natural grey hair containing 90% white hairs. The hair was then rinsed, washed with a standard shampoo and then dried.

The hair was dyed in a pearlescent ash chestnut shade which had very good fastness properties with respect to subsequent shampooing.

We claim:

1. A ready-to-use composition for the oxidation dyeing of keratin fibers comprising, in a medium suitable for dyeing:
   at least one oxidation base wherein said oxidation base is a paraphenylenediamine, a bis(phenyl)alkylenediamine, or an acid addition salt thereof,
   at least one coupler, wherein said coupler is a meta-diphenol or an acid addition salt thereof,
   at least one oxidizing agent; and
   at least one cationic direct dye (a) or (b), wherein (a) and (b) are defined as follows:
   a) the compounds of formulae (I) and (I'):
   wherein formula (I) is

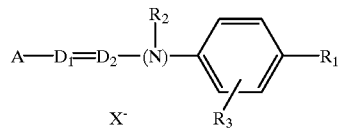

(I)

in which:
   $R_1$ represents a hydrogen atom, a $C_1$–$C_4$ alkoxy radical, a halogen atom, or an amino radical,
   $R_2$ represents a hydrogen atom, a $C_1$–$C_4$ alkyl radical or forms, with a carbon atom of the benzene ring, a heterocycle which is optionally oxygenated and/or substituted with one or more $C_1$–$C_4$ alkyl groups,
   $R_3$ represents a hydrogen or halogen atom,
   $R_4$ and $R_5$ each independently represent a hydrogen atom or a $C_1$–$C_4$ alkyl radical,
   $D_1$ and $D_2$ each independently represent a nitrogen atom or a —CH group, and m=0 or 1,
   wherein when $R_1$ represents an unsubstituted amino group, then $D_1$ and $D_2$ simultaneously represent a —CH group and m=0,
   $X^-$ represents an anion selected from chloride, metasulphate, or acetate,
   A represents a group having a structure corresponding to one of structures A1 to A8:

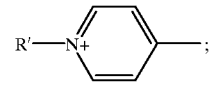

A1

-continued

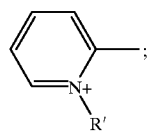
A2

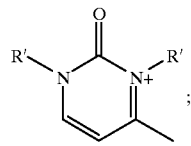
A3

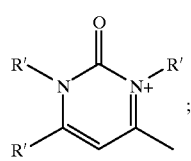
A4

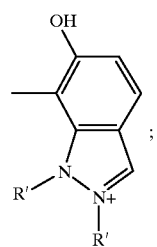
A5

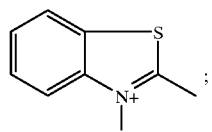
A6 or

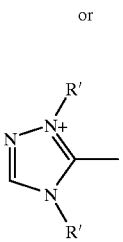
A8 in which
  $R_1$ represents a $C_1$–$C_4$ alkyl radical; and
when m=0 and $D_1$ represents a nitrogen atom, then A may also denote a group of structure A9:

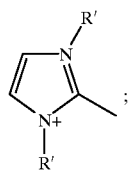
A9 in which
  $R^1$ represents a $C_1$–$C_4$ alkyl radical;

and formula (I') is

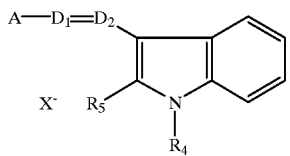
(I')

in which:
  $R_1$ represents a hydrogen atom, a $C_1$–$C_4$ alkoxy radical, a halogen atom, or an amino radical,
  $R_2$ represents a hydrogen atom, a $C_1$–$C_4$ alkyl radical or forms, with a carbon atom of the benzene ring, a heterocycle which is optionally oxygenated and/or substituted with one or more $C_1$–$C_4$ alkyl groups,
  $R_3$ represents a hydrogen or halogen atom,
  $R_4$ and $R_5$ each independently represent a hydrogen atom or a $C_1$–$C_4$ alkyl radical,
  $D_1$ and $D_2$ each independently represent a nitrogen atom or a —CH group, and m=0 or 1,
  wherein when $R_1$ represents an unsubstituted amino group, then $D_1$ and $D_2$ simultaneously represent a —CH group and m=0,
  $X^-$ represents an anion selected from chloride, metasulphate, or acetate,
  A represents a group selected from the structures A1 to A8:

A1

A2

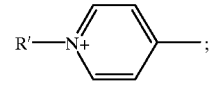

A3

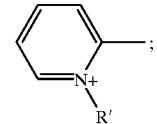

A4

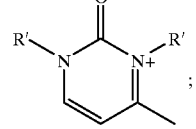

A5

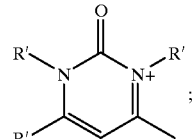

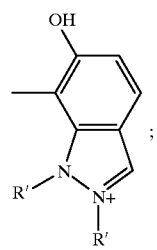

-continued

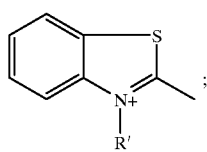
A6

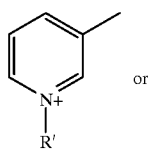
A7 or

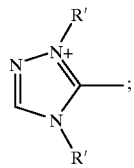
A8 in which
R¹ represents a C₁–C₄ alkyl radical; and
when m=0 and D₁ represents a nitrogen atom, then A may also denote a group of structure A9:

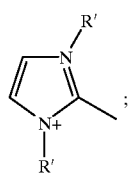
A9 in which
R¹ represents a C₁–C₄ alkyl radical; and
b) the compounds of formula (II):

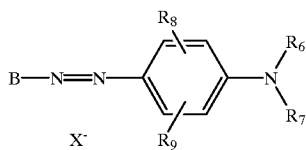
(II)

in which:
R₆ represents a hydrogen atom or a C₁–C₄ alkyl radical,
R₇ represents a hydrogen atom, an alkyl radical which may be substituted with a —CN radical or an amino group or a 4'-aminophenyl radical or forms with R₆ a heterocycle which is optionally oxygenated and/or nitrogenous, which may be substituted with one or more C₁–C₄ alkyl groups,
R₈ and R₉ each independently represent a hydrogen atom, a halogen atom, a C₁–C₄ alkyl radical, a C₁–C₄ alkoxy radical or a —CN radical,
X⁻ represents an anion selected from chloride, methylsulphate or acetate, B represents a group selected from the structures B1 to B11:

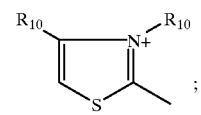
B1

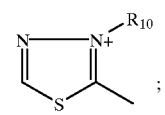
B2

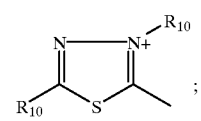
B3

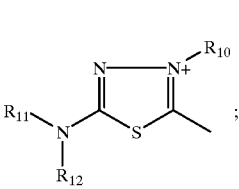
B4

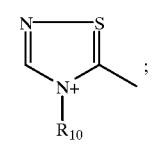
B5

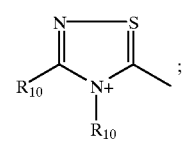
B6

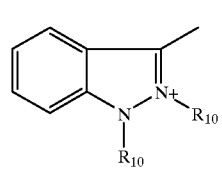
B7

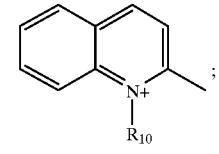
B8

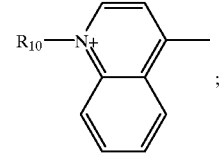
B9

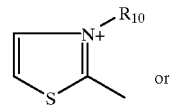
B10 or

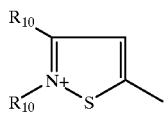

in which
R₁₀ represents a $C_1$–$C_4$ alkyl radical,
R₁₁ and R₁₂ each independently represents a hydrogen atom or a $C_1$–$C_4$ alkyl radical;
wherein when $R_6$ and $R_7$ form a nitrogenous heterocycle, or when $R_8$ and $R_9$ simultaneously represent a $C_1$–$C_4$ alkoxy radical, or when $R_7$ represents a 4'-aminophenyl radical, then B may also represent a group of structure B12:

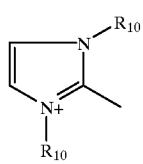

in which
$R_{10}$ represents a $C_1$–$C_4$ alkyl radical.

2. A ready-to-use composition according to claim 1, wherein said keratin fibers are human hair.

3. A ready-to-use composition according to claim 1, wherein, with respect to $R_1$, said halogen atom is bromine, chlorine, iodine or fluorine.

4. A ready-to-use composition according to claim 1, wherein, with respect to $R_3$, said halogen atom is bromine, chlorine, iodine or fluorine.

5. A ready-to-use composition according to claim 1, wherein at lest one of $R_8$ or $R_9$ independently represents bromine, chlorine, iodine or fluorine.

6. A ready-to-use composition according to claim 1, wherein said para-phenylenediamine is a compound having a structure corresponding to formula (III), or an acid-addition salt thereof:

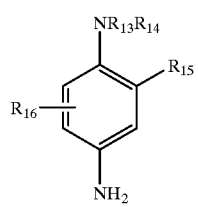

in which:
$R_{13}$ represents a hydrogen atom, a $C_1$–$C_4$ alkyl, $C_1$–$C_4$ monohydroxyalkyl, $C_2$–$C_4$ polyhydroxyalkyl, phenyl, 4'-aminophenyl or ($C_1$–$C_4$)alkoxy($C_1$–$C_4$)alkyl radical,
$R_{14}$ represents a hydrogen atom or a $C_1$–$C_4$ alkyl, $C_1$–$C_4$ monohydroxyalkyl or $C_2$–$C_4$ polyhydroxyalkyl radical,
$R_{15}$ represents a hydrogen atom, a halogen atom, or a $C_1$–$C_4$ alkyl, $C_1$–$C_4$ monohydroxyalkyl, $C_1$–$C_4$ hydroxyalkoxy, $C_1$–$C_4$ mesylaminoalkoxy, $C_1$–$C_4$ carbamoylaminoalkoxy or $C_1$–$C_4$ acetylaminoalkoxy radical, $R_{16}$ represents a hydrogen atom or a $C_1$–$C_4$ alkyl radical.

7. A ready-to-use composition according to claim 6, wherein, with respect to $R_{15}$, said halogen atom is chlorine, bromine, iodine, or fluorine.

8. A ready-to-use composition according to claim 6, wherein said para-phenylenediamine is:
para-phenylenediamine,
para-toluylenediamine,
2-chloro-para-phenylenediamine,
2,3-dimethyl-para-phenylenediamine,
2,6-dimethyl-para-phenylenediamine,
2,6-diethyl-para-phenylenediamine,
2,5-dimethyl-para-phenylenediamine,
N,N-dimethyl-para-phenylenediamine,
N,N-diethyl-para-phenylenediamine,
N,N-dipropyl-para-phenylenediamine,
4-amino-N,N-diethyl-3-methylaniline,
N,N-bis(β-hydroxyethyl)-para-phenylenediamine,
4-amino-N,N-bis(β-hydroxyethyl)-3-methylaniline,
4-amino-3-chloro-N,N-bis(β-hydroxyethyl)aniline,
2-β-hydroxyethyl-para-phenylenediamine,
2-fluoro-para-phenylenediamine,
2-isopropyl-para-phenylenediamine,
N-(β-hydroxypropyl)-para-phenylenediamine,
2-hydroxymethyl-para-phenylenediamine,
N,N-dimethyl-3-methyl-para-phenylenediamine,
N,N-(ethyl-β-hydroxyethyl)-para-phenylenediamine,
N-(β,γ-dihydroxypropyl)-para-phenylenediamine,
N-(4'-aminophenyl)-para-phenylenediamine,
N-phenyl-para-phenylenediamine,
2-β-hydroxyethyloxy-para-phenylenediamine,
2-β-acetylaminoethyloxy-para-phenylenediamine,
or an acid-addition salt thereof.

9. A ready-to-use composition according to claim 8, wherein said para-phenylenediamine is para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, N,N-bis(β-hydroxyethyl)-para-phenylenediamine, 2-β-hydroxyethyl-para-phenylenediamine, 2-β-hydroxyethyloxy-para-phenylenediamine, 2-isopropyl-para-phenylenediamine, or an acid-addition salt thereof.

10. A ready-to-use composition according to claim 1, wherein said bis(phenyl)alkylenediamine has a structure corresponding to formula (IV), or an acid-addition salt thereof:

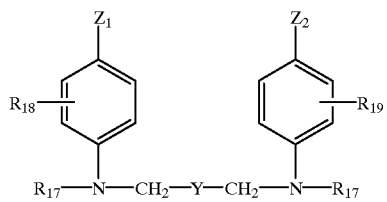

in which:
$Z_1$ and $Z_2$ each independently represents a hydroxyl radical or $NHR_{20}$ in which $R_{20}$ represents a hydrogen atom or a $C_1$–$C_4$ alkyl radical, $R_{17}$ represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical having an amino residue that can be substituted, $R_{18}$ and $R_{19}$ each independently represent a hydrogen or halogen atom or a $C_1$–$C_4$ alkyl radical, Y represents one of the following radicals:

—$(CH_2)_{\overline{n}}$—;    —$(CH_2)_{\overline{m}}$—O—$(CH_2)_{\overline{m}}$—;

—$(CH_2)_m$—CHOH—$(CH_2)_{\overline{m}}$—  or

—$(CH_2)_{\overline{m}}$—N—$(CH_2)_{\overline{m}}$—;
         |
         $CH_3$ in which:

n is an integer ranging from 0 to 8 and m is an integer ranging from 0 to 4.

11. A ready-to-use composition according to claim 10, wherein said structure corresponding to formula (IV) is:

N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, or an acid-addition salt thereof.

12. A ready-to-use composition according to claim 11, wherein said structure corresponding to formula (IV) is N,N'-bis(β-hydroxyethyl)-N,N'-bis(4'-aminophenyl)-1,3-diaminopropanol or an acid-addition salt thereof.

13. A ready-to-use composition according to claim 1, wherein said meta-diphenol is a compound of formula (V), or an acid-addition salt thereof:

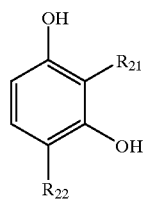
(V)

in which:

$R_{21}$ and $R_{22}$ each independently represent a hydrogen atom, a $C_1$–$C_4$ alkyl radical or a halogen atom.

14. A ready-to-use composition according to claim 13, wherein at least one of $R_{21}$ or $R_{22}$ independently represents chlorine, bromine or fluorine.

15. A ready-to-use composition according to claim 13, wherein said meta-diphenols of formula (V) is 1,3-dihydroxybenzene, 2-methyl-1,3-dihydroxybenzene, 4-chloro-1,3-dihydroxybenzene, 2-chloro-1,3-dihydroxybenzene, or an acid-addition salt thereof.

16. A ready-to-use composition according to claim 1, wherein said at least one cationic direct dye of formula (I) is a compound corresponding to one of structures (I1) to (I18):

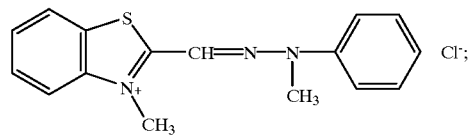
(I1)

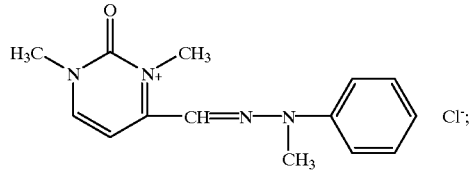
(I2)

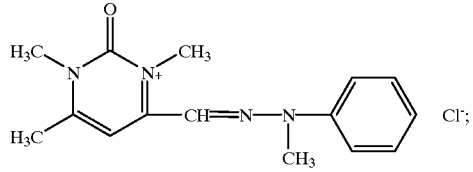
(I3)

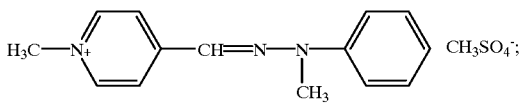
(I4)

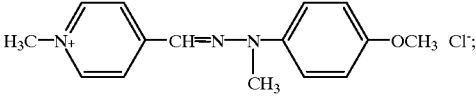
(I5)

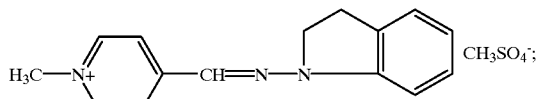
(I6)

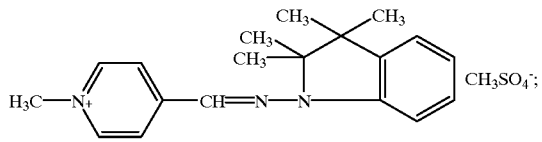
(I7)

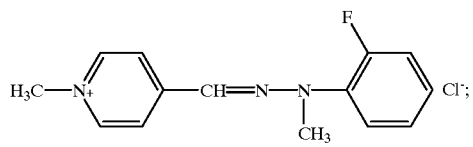
(I8)

17. A ready-to-use composition according to claim 1, wherein said at least one cationic direct dye of formula (I') is a compound corresponding to one of structures (I'1) to (I'3):

18. A ready-to-use composition according to claim 1, wherein said at least one cationic direct dye of formula (II) is a compound corresponding to one of structures (II1) to (II26):

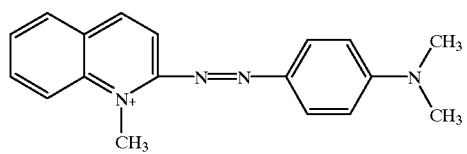 (II3) Cl⁻;
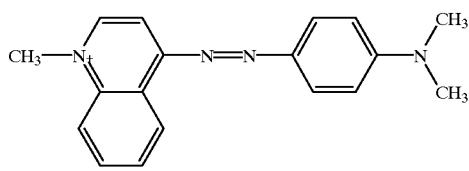 (II4) Cl⁻;
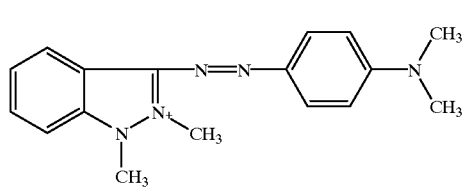 (II5) Cl⁻;
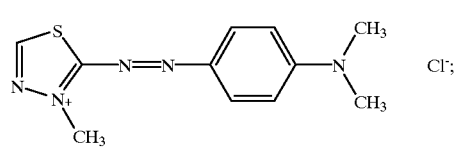 (II6) Cl⁻;
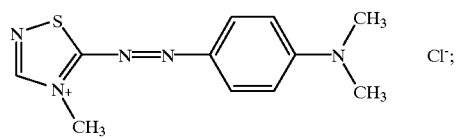 (II7) Cl⁻;
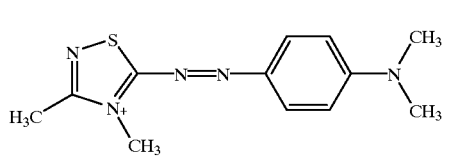 (II8) Cl⁻;
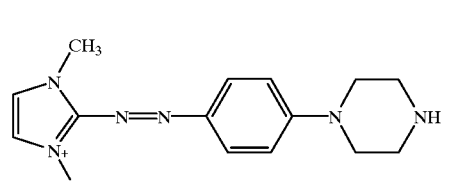 (II9) Cl⁻;
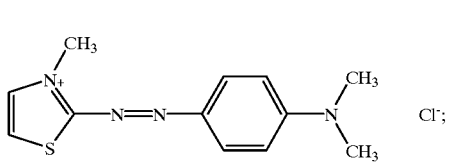 (II10) Cl⁻;
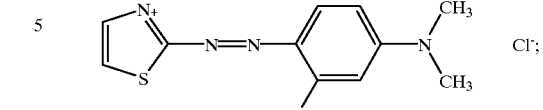 (II11) Cl⁻;
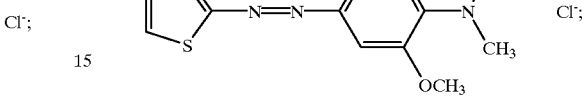 (II12) Cl⁻;
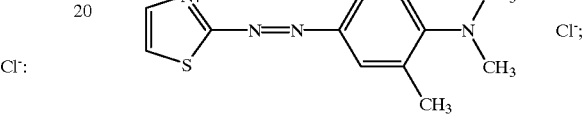 (II13) Cl⁻;
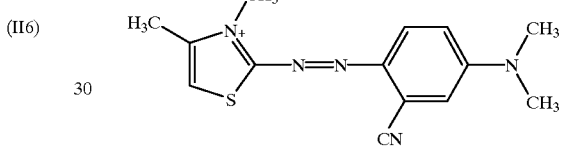 (II14) Cl⁻;
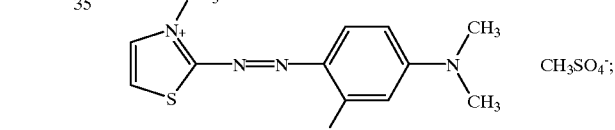 (II15) CH₃SO₄⁻;
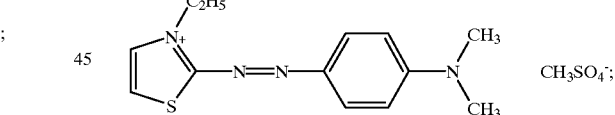 (II16) CH₃SO₄⁻;
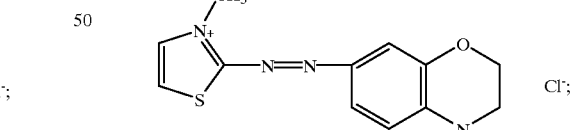 (II17) Cl⁻;
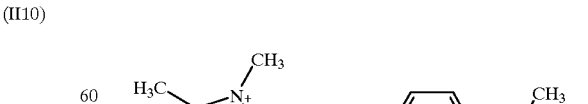 (II18) CH₃SO₄⁻;

-continued

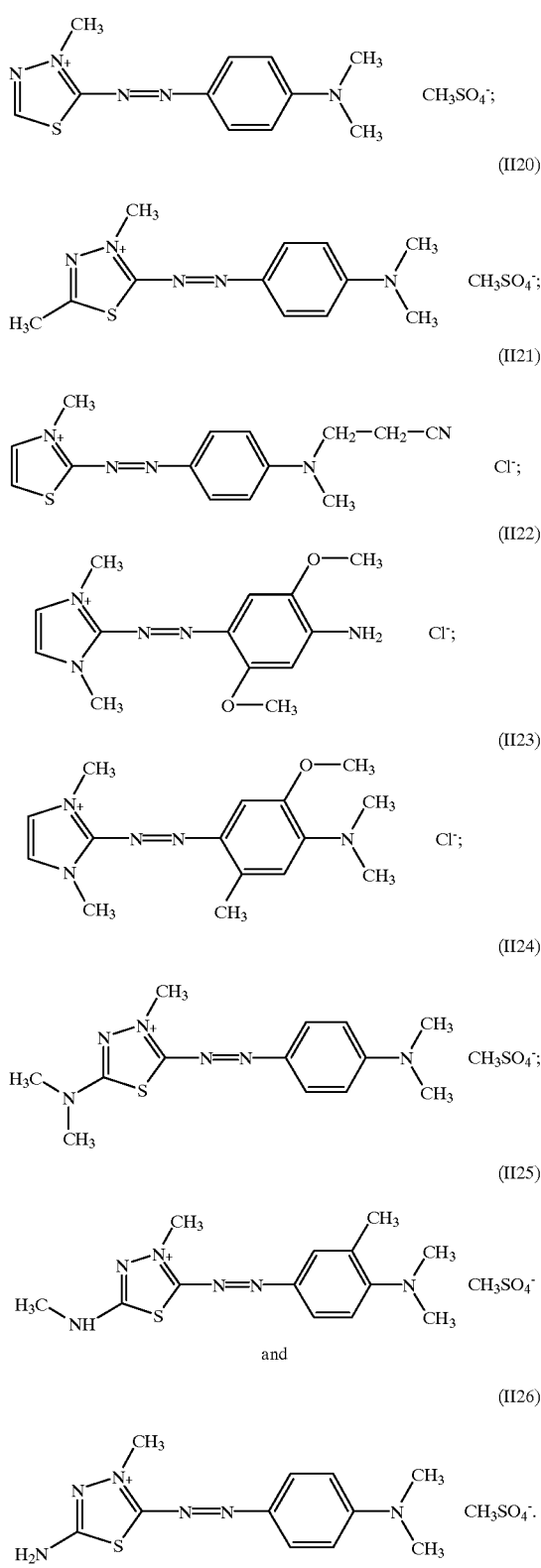

19. A ready-to-use composition according to claim 16, wherein said at least one cationic direct dye of formula (I) is a compound corresponding to structure (I1), (I5) or (I13).

20. A ready to use composition according to claim 18, wherein said at least one cationic dye of formula (II) corresponds to structure (II1).

21. A ready-to-use composition according to claim 1, wherein said acid-addition salt of said at least one oxidation base or said at least one coupler is a hydrochloride, carbonate, hydrobromide, sulphate or tartrate.

22. A ready-to-use composition according to claim 1, wherein said at least one oxidizing agent is hydrogen peroxide, urea peroxide, an alkali metal bromate or a persalt.

23. A ready-to-use composition according to claim 22, wherein said persalt is a perborate or a persulphate.

24. A ready-to-use composition according to claim 22, wherein said at least one oxidizing agent is hydrogen peroxide.

25. A ready-to-use composition according to claim 1, wherein said at least one cationic direct dye is present in a concentration ranging from 0.001 to 10% by weight relative to the total weight of the ready-to-use dye composition.

26. A ready-to-use composition according to claim 25, wherein said at least one cationic direct dye is present in a concentration ranging from 0.05 to 2% by weight relative to the total weight of the ready-to-use composition.

27. A ready-to-use composition according to claim 1, wherein said at least one oxidation base is present in a concentration ranging from 0.0001 to 10% by weight relative to the total weight of the ready-to-use composition.

28. A ready-to-use composition according to claim 1, wherein said at least one coupler is present in a concentration ranging from 0.0001 to 5% by weight relative to the total weight of the ready-to-use composition.

29. A ready-to-use composition according to claim 1, wherein said ready-to-use composition has a pH ranging from 5 to 12.

30. A ready-to-use composition according to claim 1, wherein said medium suitable for dyeing comprises water or a mixture of water and at least one organic solvent.

31. A ready-to-use composition according to claim 30, wherein said at least one organic solvent is present in a concentration ranging from 1 to 40% by weight, relative to the total weight of the ready-to-use composition.

32. A process for dyeing keratin fibers comprising applying at least one ready-to-use composition according to claim 1 to said keratin fibers.

33. A process according to claim 32, wherein said keratin fibers are human hair.

34. A process for dyeing keratin fibers according to claim 32, wherein said ready-to-use dye composition is left on said keratin fibers for a time ranging from 3 to 40 minutes, and then is rinsed, optionally washed with shampoo, rinsed again and dried.

35. A process for dyeing keratin fibers according to claim 34, wherein said ready-to-use dye composition is left on said keratin fibers for a time ranging from 5 to 30 minutes.

36. A process for dyeing keratin fibers comprising:
  applying at least one ready-to-use composition according to claim 1 to said keratin fibers, wherein said process further comprises the preliminary steps of:
    preparing a composition (A) comprising, in a medium which is suitable for dyeing, at least one oxidation base according to claim 1, at least one coupler according to claim 1, and at least one cationic direct dye according to claim 1,
    separately preparing a composition (B) comprising, in a medium which is suitable for dyeing, at least one oxidizing agent according to claim 1,
    separately storing composition (A) from composition (B), and mixing said composition (A) and said composition (B) together at the time of application before applying to said keratin fibers.

37. A process for dyeing keratin fibers comprising applying at least one ready-to-use composition according to claim 1 to said keratin fibers, wherein said process further comprises the preliminary steps of:
- preparing a composition (A) comprising, in a medium which is suitable for dyeing, at least one oxidation base according to claim 1 and at least one coupler according to claim 1,
- separately preparing a composition (A') comprising, in a medium which is suitable for dyeing, at least one cationic direct dye according to claim 1,
- separately preparing a composition (B) comprising, in a medium which is suitable for dyeing, at least one oxidizing agent according to claim 1, and
- mixing said composition (A), said composition (A'), and said composition (B) together at the time of application before applying to said keratin fibers.

38. A process according to claim 37, wherein said composition (A') is in powder form.

39. A multi-compartment dyeing kit or device, wherein said multi-compartment dyeing kit or device comprises a first compartment containing a composition (A) comprising, in a medium which is suitable for dyeing, at least one oxidation base according to claim 1, at least one coupler according to claim 1, and at least one cationic direct dye according to claim 1, and a second compartment containing an oxidizing composition (B) comprising, in a medium which is suitable for dyeing, at least one oxidizing agent according to claim 1.

40. A multi-compartment dyeing kit or device, wherein said multi-compartment dyeing kit or device comprises a first compartment containing a composition (A) comprising, in a medium which is suitable for dyeing, at least one oxidation base according to claim 1 and at least one coupler according to claim 1, a second compartment containing a composition (A') comprising, in a medium which is suitable for dyeing, at least one cationic direct dye according to claim 1, and a third compartment containing an oxidizing composition (B) comprising, in a medium which is suitable for dyeing, at least one oxidizing agent according to claim 1.

41. A ready-to-use compositions according to claim 1, wherein said composition is in the form of a liquid, a cream, a gel, or any form appropriate for dyeing keratin fibers.

* * * * *

UNITED STATES PATENT AND TRADEMARK OFFICE
CERTIFICATE OF CORRECTION

PATENT NO. : 5,993,490

DATED : November 30, 1999

INVENTOR(S) : RONDEAU et al.

It is certified that error appears in the above-identified patent and that said Letters Patent is hereby corrected as shown below:

In claim 1, column 19, lines 52 and 67, "$R_1$" and "$R^1$" should read --R'--;

column 21, lines 29 and 43, "$R^1$" should read --R'--;

Title page, item [75], line 3, "le Vesinet" should read --Le Vesinet--.

Signed and Sealed this

Twentieth Day of June, 2000

*Attest:*

Q. TODD DICKINSON

*Attesting Officer*    *Director of Patents and Trademarks*